United States Patent
Nagase

(10) Patent No.: US 8,135,371 B2
(45) Date of Patent: Mar. 13, 2012

(54) RECEIVING APPARATUS AND RECEIVING SYSTEM

(75) Inventor: Ayako Nagase, Tokyo (JP)

(73) Assignee: Olympus Corporation, Tokyo (JP)

( * ) Notice: Subject to any disclaimer, the term of this patent is extended or adjusted under 35 U.S.C. 154(b) by 1156 days.

(21) Appl. No.: 11/631,069

(22) PCT Filed: Sep. 29, 2005

(86) PCT No.: PCT/JP2005/017993
§ 371 (c)(1),
(2), (4) Date: Dec. 28, 2006

(87) PCT Pub. No.: WO2006/038524
PCT Pub. Date: Apr. 13, 2006

(65) Prior Publication Data
US 2009/0191830 A1    Jul. 30, 2009

(30) Foreign Application Priority Data
Oct. 1, 2004    (JP) ................................. 2004-290689

(51) Int. Cl.
*H04B 1/06*    (2006.01)
*H04M 1/00*    (2006.01)

(52) U.S. Cl. ....................... 455/277.2; 455/557; 600/128

(58) Field of Classification Search ............... 455/67.11, 455/67.13, 269, 272, 277.1, 277.2, 296, 344, 455/556.1, 566, 557; 600/128, 160, 476
See application file for complete search history.

(56) References Cited

U.S. PATENT DOCUMENTS

| 5,029,233 | A | * | 7/1991 | Metroka | 455/552.1 |
| 5,857,151 | A | * | 1/1999 | Heinonen et al. | 455/321 |
| 6,951,536 | B2 | * | 10/2005 | Yokoi et al. | 600/128 |
| 7,260,382 | B1 | * | 8/2007 | Lamb et al. | 455/411 |
| 7,454,545 | B2 | * | 11/2008 | Kohno et al. | 379/93.03 |

(Continued)

FOREIGN PATENT DOCUMENTS
EP    1 124 211 A2    8/2001
(Continued)

OTHER PUBLICATIONS

Extended Supplementary European Search Report dated Nov. 26, 2009.

*Primary Examiner* — Quochien B Vuong
(74) *Attorney, Agent, or Firm* — Scully, Scott, Murphy & Presser, P.C.

(57) ABSTRACT

A receiving apparatus (2) includes a radio unit (2a) and a main receiving unit (2b) detachably connected with each other, the radio unit (2a) stores radio unit ID information (12a) as identification information to identify the radio unit itself, the main receiving unit (2b) stores a process condition table (16a) in which process conditions corresponding to the radio units are stored, the main receiving unit (2b) includes a setting controller (C1b) which serves as a setting controller that sets the process condition of the main receiving unit (2b), the setting controller (C1b) acquires the radio unit ID information (12a) from the radio unit (2a), selects the process condition of the main receiving unit (2b) corresponding to the acquired radio unit ID information (12a) from the process condition table (16a), and sets the selected process condition as the process condition of the main receiving unit (2b), so that, when a replaceable unit detachably connected to a shared unit is replaced with another replaceable unit, a process condition of the shared unit can be securely set for each replaceable unit.

6 Claims, 6 Drawing Sheets

U.S. PATENT DOCUMENTS

| | | |
|---|---|---|
| 2002/0173718 A1 | 11/2002 | Frisch et al. |
| 2002/0184122 A1 | 12/2002 | Yamaguchi et al. |
| 2003/0023150 A1 | 1/2003 | Yokoi et al. |
| 2003/0085994 A1 | 5/2003 | Fujita et al. |
| 2003/0213495 A1 | 11/2003 | Fujita et al. |
| 2004/0111011 A1 | 6/2004 | Uchiyama et al. |
| 2005/0004473 A1 | 1/2005 | Fujita et al. |
| 2005/0194012 A1 | 9/2005 | Ito et al. |
| 2005/0195118 A1 | 9/2005 | Ito et al. |

FOREIGN PATENT DOCUMENTS

| | | |
|---|---|---|
| JP | 2003-19111 | 1/2003 |
| JP | 2003-325439 | 11/2003 |
| JP | 2004-167163 | 6/2004 |
| JP | 2005-143668 | 6/2005 |
| JP | 2005-192821 | 7/2005 |
| JP | 2005-245938 | 9/2005 |
| WO | WO 2005/065524 A1 | 7/2005 |

* cited by examiner

FIG.4

| RADIO UNIT ID | | | | | PROCESS CONDITION OF PROCESS PERFORMED BY MAIN RECEIVING UNIT | | | | |
|---|---|---|---|---|---|---|---|---|---|
| TYPE ID | STATE ID | NUMBER ID | FRAME RATE ID | SERIAL ID | ANTENNA SWITCHING | DISPLAY | LANGUAGE | NUMBER OF ANTENNAS | PROCESS SPEED |
| 01 | JP | 00 | 00 | 00 | ON | OFF | JAPANESE | 10 | 2 |
| 01 | JP | 01 | 01 | 01 | | | | 8 | 4 |
| 01 | JP | 00 | 00 | 02 | | | | 10 | 2 |
| ... | ... | ... | ... | ... | | | | ... | ... |
| 01 | US | 00 | 00 | 20 | ON | OFF | ENGLISH | 10 | 2 |
| 01 | US | 01 | 01 | 21 | | | | 8 | 4 |
| ... | ... | ... | ... | ... | | | | ... | ... |
| 02 | JP | 11 | 11 | 40 | OFF | ON | JAPANESE | 1 | 25 |
| 02 | JP | 11 | 11 | 41 | | | | 1 | 25 |
| ... | ... | ... | ... | ... | | | | ... | ... |

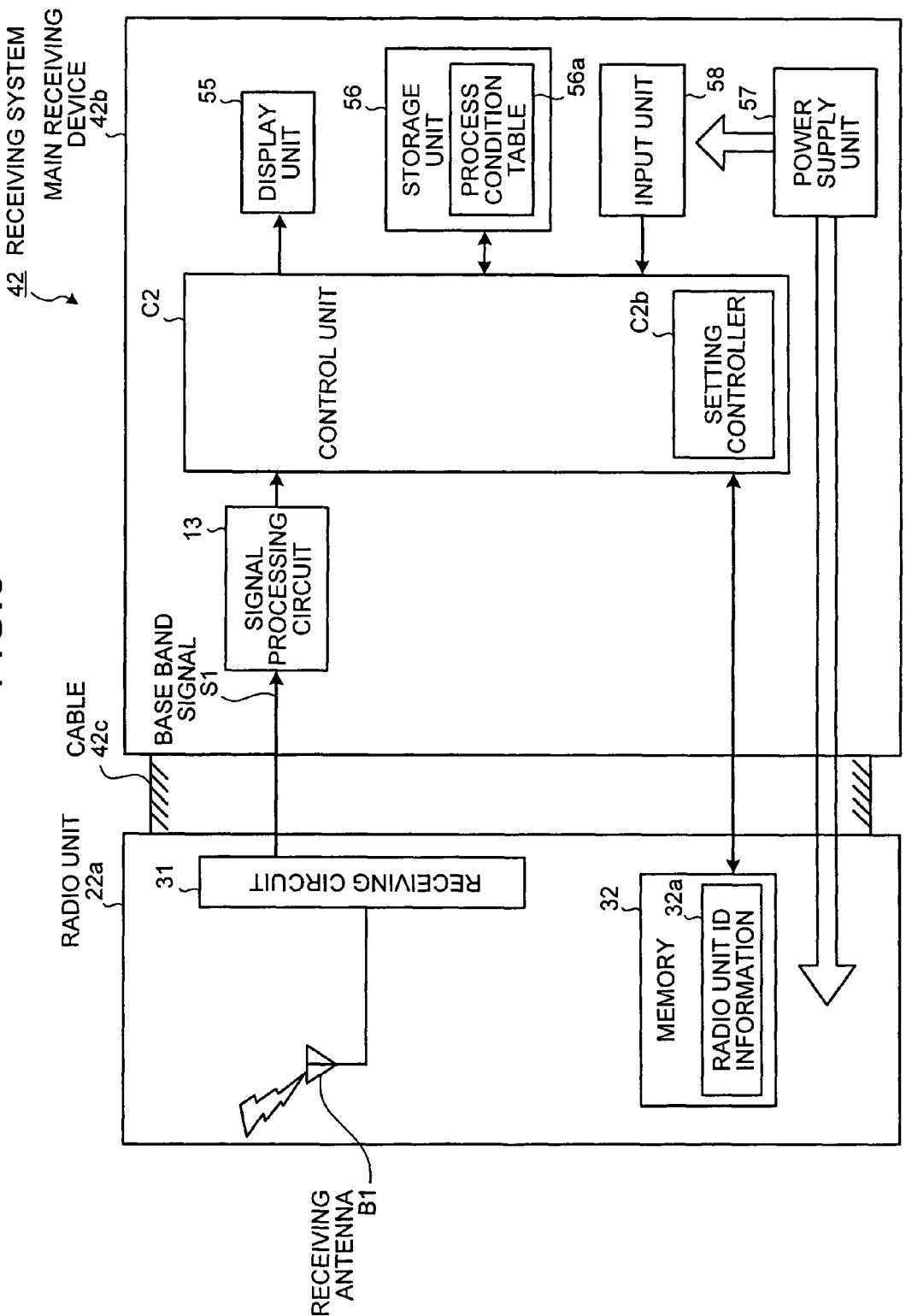

RECEIVING APPARATUS AND RECEIVING SYSTEM

TECHNICAL FIELD

The present invention relates to a receiving apparatus and a receiving system that demodulate radio signals received by antenna(s) into base band signals, and acquire transmission information based on the base band signals obtained as a result of demodulation, and more particularly to a receiving apparatus and a receiving system that receive radio signals transmitted from a capsule endoscope inside a subject by using antenna(s) provided outside the subject.

BACKGROUND ART

In recent years, swallowable capsule endoscopes are being developed in a field of endoscope. The capsule endoscope is equipped with an imaging function and a radio communication function. After being swallowed by a patient for an observation of an interior of a body cavity, the capsule endoscope travels through inside organs such as esophagus, stomach, and small intestine following peristaltic movements and sequentially captures images until naturally discharged from a human body.

Image data obtained inside the body cavities by the capsule endoscope while traveling inside the body cavities is sequentially transmitted to an outside of the subject by radio communication, and either accumulated in a memory arranged in a receiver disposed outside the subject, or displayed on a display unit included in the receiver. A doctor and a nurse can make diagnosis based on images presented on the display unit by looking at the images displayed based on the image data accumulated in the memory or by looking at the images displayed on the display unit in the receiver simultaneously with the image data reception.

When the receiver is configured to have a memory for accumulation of the image data, the receiver in general is provided with plural antennas for receiving image signals transmitted from the capsule endoscope. The plural antennas are arranged outside the subject in a dispersed manner, and the receiver selects an antenna whose received strength is high from the plural antennas and receives the image signals by the selected antenna by switching. For example, Patent Document 1 describes a receiver which switches over plural antennas arranged outside the subject and locates the capsule endoscope, i.e., an image signal sender, in the subject based on electric field strength received by each antenna.

Patent Document 1: Japanese Patent Application Laid-Open No. 2003-19111

DISCLOSURE OF INVENTION

Problem to be Solved by the Invention

Usable frequency for the radio signals transmitted from the capsule endoscope is different from country to country. Therefore, conventionally, different dedicated receivers are manufactured for each country. Further, different receivers have to be manufactured depending on the use, for example, whether the image data is accumulated in the memory after the reception, or the image data is displayed on the display unit in the receiver simultaneously with the reception.

In view of the foregoing, an object of the present invention is to provide a receiving system whose overall configuration includes a replaceable unit that includes elements to be replaced depending on a state where the system is used, purpose of use, and the like, and a shared unit that includes commonly-usably elements, and the replaceable unit and the shared unit are detachably connected with each other, so that only the replaceable unit can be replaced depending on the purpose, that process conditions of the shared unit can be securely set every time the replaceable unit is replaced, whereby desirable information can be surely obtained.

Means for Solving Problem

A receiving apparatus according to the present invention includes a radio unit which includes a storing unit which stores identification information for identification of the radio unit, and demodulates radio signals received by antennas into base band signals; and a main receiving unit which includes a storage table in which process conditions of processes performed by the main receiving unit are stored in advance corresponding to each radio unit, and a setting controller which, when the radio unit is connected to the main receiving unit, acquires the identification information, selects the process condition corresponding to the identification information acquired by referring to the storage table, and sets the selected process condition as a process condition of the process performed by the main receiving unit, the main receiving unit performing at least a process to acquire information transmitted from the radio unit based on the base band signals.

In the receiving apparatus according to the present invention, the main receiving unit may include a switching controller which controls switching-over of the antennas based on signal strength of the radio signal received by each of the antennas, and the setting controller may set a process condition for controlling the switching-over of the antennas by the switching controller as the process condition based on information stored in the storage table concerning a number of the antennas.

In the receiving apparatus according to the present invention, the main receiving unit may include an image display unit which displays image information based on the information transmitted from the radio unit, and the setting controller may set a process condition for displaying the image information on the image display unit as the process condition based on information stored in the storage table concerning a manner of output of the image information.

In the receiving apparatus according to the present invention, the main receiving unit may include a processor which performs processes at variable process speed on the information transmitted from the radio unit, and the setting controller may set a process speed of the processor based on information stored in the storage table concerning a transmission rate of the information transmitted.

A receiving system according to the present invention includes a radio device which includes a storing unit which stores identification information for identification of the radio device, and demodulates radio signals received by an antenna into base band signals; a main receiving device which includes a storage table in which process conditions of processes performed by the main receiving device are stored in advance corresponding to each radio device, and a setting controller which, when the radio device is connected to the main receiving device, acquires the identification information, selects the process condition corresponding to the identification information acquired by referring to the storage table, and sets the selected process condition as a process condition of the process performed by the main receiving device, the main receiving device performing at least a process to acquire information transmitted from the radio device based on the base band signals; and a connector which connects the radio device and the main receiving device with each other.

In the receiving system according to the present invention, the main receiving device may include an image display unit which displays image information based on the information transmitted from the radio device, and the setting controller may set a process condition for displaying the image information on the image display unit as the process condition based on information stored in the storage table concerning a manner of output of the image information.

Effect of the Invention

The receiving apparatus and the receiving system according to the present invention has an overall structure including the replaceable unit and the shared unit detachably connected with each other so that only the replaceable unit can be replaced depending on the purpose, and that the process condition of the shared unit can be surely set each time the replaceable unit is replaced, whereby desirable information can be surely obtained.

BRIEF DESCRIPTION OF DRAWINGS

FIG. 4 is an example of a process condition table shown in FIGS. 1 and 2;

FIG. 6 is a block diagram of a structure of a receiving system shown in FIG. 5.

EXPLANATIONS OF LETTERS OR NUMERALS

Figure 1:
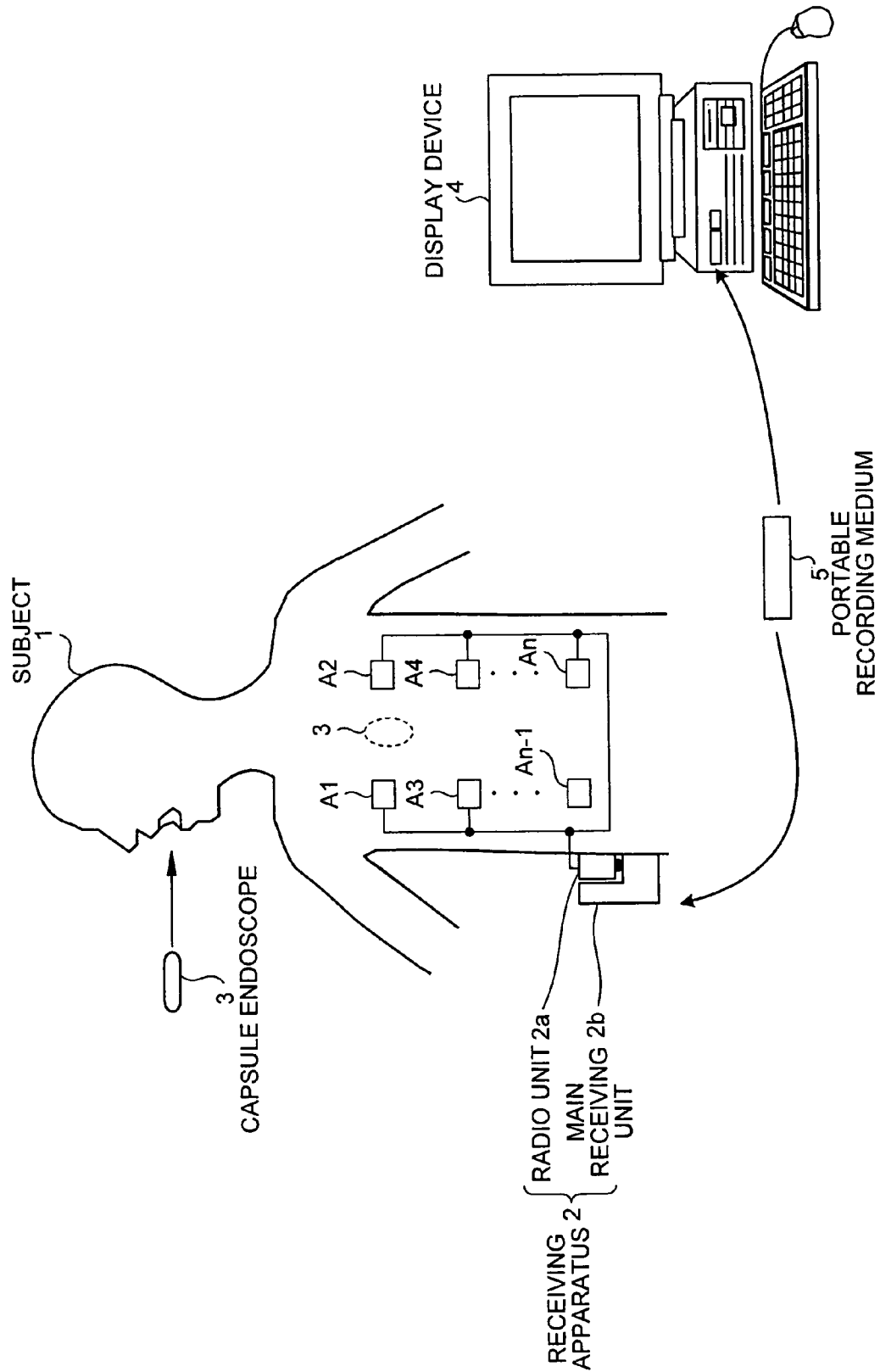
FIG. 1 is a schematic diagram of an overall structure of a wireless in-vivo information acquiring system according to a first embodiment of the present invention.

1 Subject
2, 22 Receiving apparatus
2a, 22a Radio unit
2b Main receiving unit
3 Capsule endoscope
4 Display device
5 Portable recording medium
11, 31 Receiving circuit
12, 32 Memory
12a, 32a Radio unit ID information
13 Signal processing circuit
14 A/D converter
15, 55 Image display unit
16, 56 Storage unit
16a, 56a Process condition table
17, 57 Power supply unit
42 Reception system
42b Main receiving device
42c Cable
58 Input unit
A1 to An, B1 Receiving antenna
C1, C2 Control unit
C1a Switching controller
C1b, C2b Setting controller
SW Changeover switch

BEST MODE(S) FOR CARRYING OUT THE INVENTION

Exemplary embodiments of a receiving apparatus and a receiving system of the present invention, in particular a wireless in-vivo information acquiring system will be described below with reference to the accompanying drawings. It should be noted that the present invention is not limited to the embodiments. In the drawings and the description, the same elements are denoted by the same reference characters.

First Embodiment

FIG. 1 is a schematic diagram of an overall structure of a wireless in-vivo information acquiring system. The wireless in-vivo information acquiring system includes a capsule endoscope as an example of a body insertable device, which works as a transmitter. As shown in FIG. 1, the wireless in-vivo information acquiring system includes a capsule endoscope 3 which is introduced inside a body of a subject 1, captures images inside body cavities, and transmits data such as image signals to a receiving apparatus 2 by radio, the receiving apparatus 2 which receives image data of an interior of the body cavities when the image data is transmitted from the capsule endoscope 3 by radio, a display device 4 which displays the image inside the body cavities based on the image signals received by the receiving apparatus 2, and a portable recording medium 5 which serves for data transfer between the receiving apparatus 2 and the display device 4. Further, the receiving apparatus 2 includes a radio unit 2a which has plural receiving antennas A1 to An pasted onto an outer surface of the subject 1 body, and a main receiving unit 2b which performs, for example, processing of radio signals received by the plural receiving antennas A1 to An. The radio unit 2a and the main receiving unit 2b are connected with each other in a detachable manner via, for example, a connector. Each of the receiving antennas A1 to An is, for example, arranged on a jacket which the subject 1 can wear. The subject 1 may put the receiving antennas A1 to An onto his/her body by wearing the jacket. The receiving antennas A1 to An may be detachable from the jacket.

The display device 4 displays images inside the body cavities captured by the capsule endoscope 3. The display device 4 has a configuration like a workstation which displays images based on data obtained from the portable recording medium 5. Specifically, the display device 4 may directly output the images as in a Cathode Ray Tube (CRT) display, a liquid crystal display, or alternatively, may output the image onto other media as in a printer.

The portable recording medium 5 includes a Compact Flash (Registered Trademark) memory, for example. The portable recording medium 5 can be attached to and detached from the main receiving unit 2b and the display device 4. When the portable recording medium 5 is attached to one of the main receiving unit 2b and the display device 4, information can be output from or recorded into the portable recording medium 5. Specifically, while the capsule endoscope 3 travels through the body cavities of the subject 1, the portable recording medium 5 is attached to the main receiving unit 2b, and the data transmitted from the capsule endoscope 3 is recorded into the portable recording medium 5. After the capsule endoscope 3 is discharged from the subject 1, in other words, after the imaging inside the subject 1 is finished, the portable recording medium 5 is removed from the main receiving unit 2b and attached to the display device 4. Then the display device 4 reads out the recorded data. When the data transfer between the main receiving unit 2b and the display device 4 is performed by the portable recording medium 5, the subject 1 can mover freely during the imaging in the body cavities, and in addition, the time required for data transfer to the display device 4 can be shortened. Alternatively, an embedded type of recording device may be arranged in the main receiving unit 2b, and the recording device may be connected with the display device 4 with a cable or by radio for data transfer between the main receiving unit 2b and the display device 4.

Figure 2:
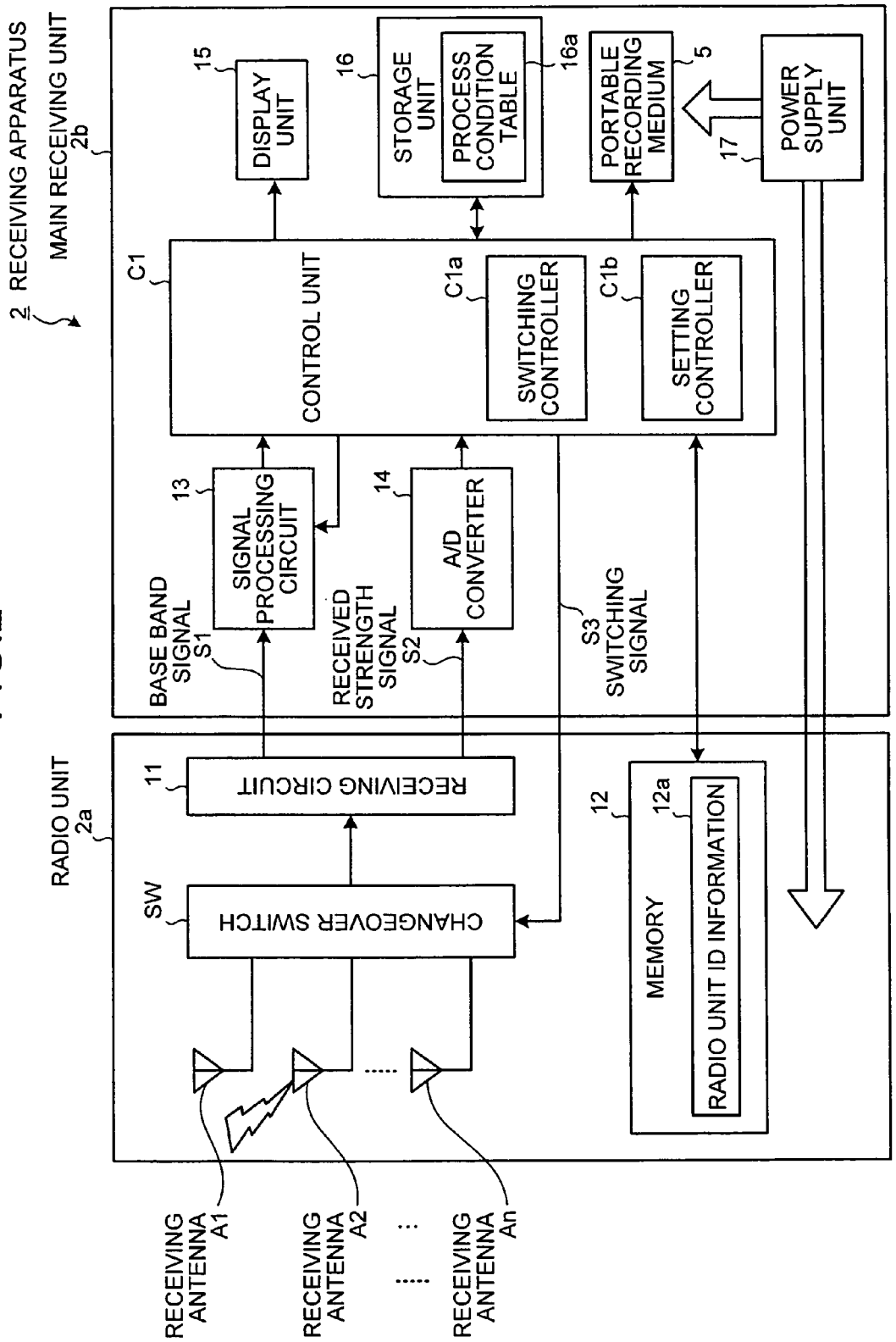
FIG. 2 is a block diagram of a structure of a receiving apparatus shown in FIG. 1.

With reference to FIG. 2, the radio unit 2a and the main receiving unit 2b will be described. FIG. 2 is a block diagram of a structure of the receiving apparatus 2. The radio unit 2a receives the radio signals transmitted from the capsule endoscope 3 and demodulates the same into base band signals. As shown in FIG. 2, the radio unit 2a includes a changeover switch SW which performs a connection switching process to selectively switches to one of the receiving antennas A1 to An, a receiving circuit 11 which is connected in a subsequent stage of the changeover switch SW to amplify and demodulate the radio signals received by one of the receiving antennas A1 to An that is connected by the changeover switch SW, and a memory 12 which serves as a storing unit. In the memory 12, radio unit ID information 12a is stored as identification information to identify the radio unit in which the memory resides.

The main receiving unit 2b receives and processes the based band signals after the demodulation in the radio unit 2a. As shown in FIG. 2, the main receiving unit 2b includes a signal processing circuit 13 and an A/D converter 14 each connected in a subsequent stage of the receiving circuit 11, a display unit 15 which displays image data processed in the signal processing circuit 13, a storage unit 16 which stores various types of information, the portable recording medium 5, a control unit C1 which controls respective elements mentioned above, and a power supply unit 17 which supplies power to the main receiving unit 2b and the radio unit 2a. The signal processing circuit 13 is a processor whose process speed of signals is variable. The signal processing circuit includes a unit to change the process speed of the signals, for example, a Phase Locked Loop (PLL). The control unit C1 includes a switching controller C1a which serves as a switching controller to control the switching of the antennas, and a setting controller C1b which serves as a setting controller to set a process condition of the process performed by the main receiving unit 2b. The storage unit 16 includes a process condition table 16a which is a storage table in which process conditions of the processes performed by the main receiving unit 2b are stored in association with the radio unit ID information 12a.

The receiving circuit 11 amplifies and demodulates the radio signals supplied from the changeover switch SW, and outputs a resulting base band signal S1 to the signal processing circuit 13, and at the same time outputs a received strength signal S2 which indicates strength of the amplified radio signal to the A/D converter 14. The image data processed by the signal processing circuit 13 is stored in the portable recording medium 5 under the control of the control unit C1, and displayed on the display unit 15 as necessary. The received strength signal S2 is converted into a digital signal in the A/D converter 14 and the resulting digital signal is taken into the control unit C1. The switching controller C1a obtains the received strength signal S2 for each of the receiving antennas A1 to An via sequential switching-over, and selects a receiving antenna which receives a signal with a highest strength as a receiving antenna for acquisition of the image data based on the received strength signals S2. At the same time, the switching controller C1a supplies a switching signal S3 to instruct the changeover switch SW to change over to the pertinent antenna. The control unit C1 stores the signal strength received by each receiving antenna together with the image data in association with the selected receiving antenna in the portable recording medium 5. The stored signal strength of each of the receiving antennas serves as information for calculation of the intra-subject position where the capsule endoscope 3 resides when the image data is received.

The setting controller C1b acquires the radio unit ID information 12a from the radio unit 2a as the identification information to identify the connected radio unit. Then, the setting controller C1b selects a process condition corresponding to the acquired radio unit ID information 12a from the process condition table 16a by referring to the process condition table 16a stored in the main receiving unit 2b. The setting controller C1b sets the selected process condition as the process condition for a process to be performed by the main receiving unit 2b. Here, the process condition of the main receiving unit 2b means various setting conditions of processes performed by the main receiving unit 2b for various radio units that are employed under different use conditions, for example, in different countries, for different purposes, for reception of image information sent at different frame rates, etc. The process conditions corresponding to various radio units which can be connected to the main receiving unit 2b are stored in the process condition table 16a in advance in association with the radio unit ID. The setting controller C1b selects, for example, a process condition to turn on the antenna connection switching process by the changeover switch SW from the process condition table 16a as the process condition corresponding to the radio unit ID information 12a, to make the switching controller C1a performs the antenna connection switching process.

Figure 3:
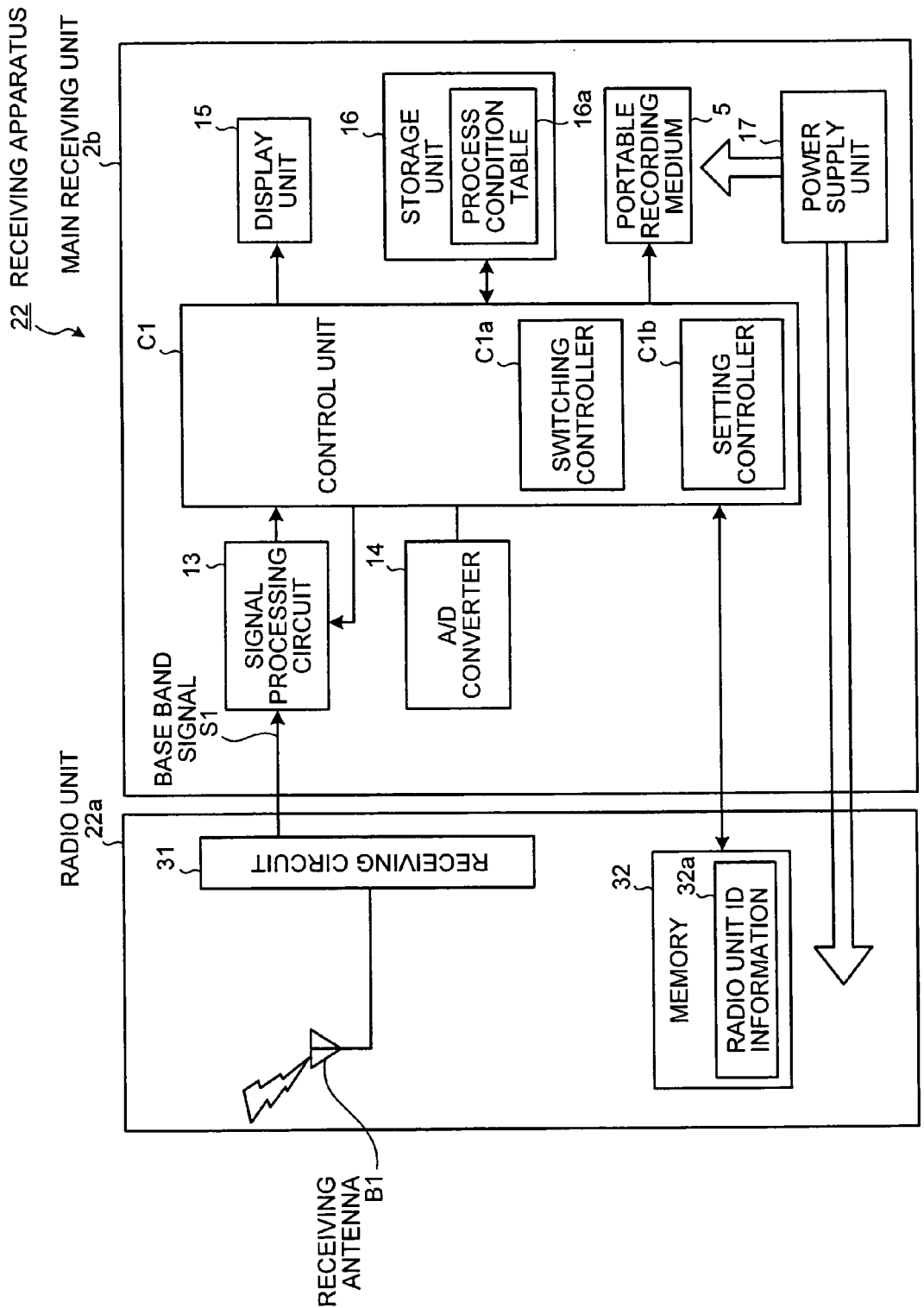
FIG. 3 is a block diagram of another structure of the receiving apparatus according to the first embodiment.

The radio unit 2a can be replaced with a radio unit 22a of a different type, as shown in FIG. 3. The number of antennas in the radio unit 22a is different from that of the radio unit 2a. The radio unit 22a includes one receiving antenna B1, a receiving circuit 31, and a memory 32. In the memory 32, radio unit ID information 32a is stored. The receiving antenna B1 is directly connected to the receiving circuit 31. The receiving circuit 31 amplifies and demodulates radio signals received by the receiving antenna B1 and supplies resulting base band signals S1 to the signal processing circuit 13. When the radio unit 22a is connected to the main receiving unit 2b, the setting controller C1b may select a process condition to display image data processed by the signal processing circuit 13 on the display unit 15 from the process condition table 16a as the process condition corresponding to the radio unit ID information 32a, for example.

With referent to FIG. 4, the process conditions set by the setting controller C1b based on the radio unit ID information for the main receiving unit 2b will be described in detail. FIG. 4 shows an example of the process condition table 16a which indicates correspondence between the radio unit ID as an identification of each radio unit and a process condition of the main receiving unit 2b. The process condition table of FIG. 4 shows the radio unit ID on the left and the process condition of the main receiving unit 2b on the right corresponding to each radio unit ID of the radio unit which may be connected to the main receiving unit 2b. As shown in FIG. 4, the radio unit ID is represented by concatenated five IDs, each representing a type ID, a state ID, a number ID, a frame rate ID, and a serial ID, for example. The type ID includes information that indicates whether the radio unit has plural receiving antenna or not, whether the image data acquired from the capsule endoscope 3 is to be recorded in the portable recording medium 5 or displayed on a screen of the display unit 15. The state ID includes information that indicates a state or a region where the radio unit is to be used; and the number ID includes information that indicates the number of receiving antennas in the radio unit. Further, the frame rate ID includes information that indicates the frame rate of the image information received by the radio unit; and the serial ID includes information that indicates a specific radio unit. The frame rate of the image information received by the radio unit is equal to a frame rate of the image information captured and transmitted by the capsule endoscope 3, and also equal to a transmission rate of the information transmitted from the radio unit to the main receiving unit 2b.

On the other hand, the process conditions of the main receiving unit 2b is, for example, whether to turn the antenna switching process by the switching controller C1a ON or OFF, whether to turn the display of the image data acquired from the capsule endoscope 3 ON or OFF, whether to display the language in Japanese or in English, on how many receiving antennas the main receiving unit 2b has to perform processing, and a process speed of the image data, as shown in FIG. 4. The setting controller C1b determines whether to turn the antenna switching process ON or OFF based on the type ID, and recognizes how many receiving antennas need switching based on the number ID. Further, the setting controller C1b determines whether to store the image data acquired from the capsule endoscope 3 in the portable recording medium 5 or to display the same on the screen based on the type ID, and determine whether to display the language in Japanese, English, or other language, based on the state ID. Further, the setting controller C1b sets the process speed of the image data processed by the signal processing circuit 13 based on the frame rate ID.

Specifically, when the radio unit ID is "01JP000000" as shown in FIG. 4, the setting controller C1b recognizes that the radio unit has plural receiving antennas based on the type ID "01", and turns the antenna switching processing ON, and turns the image data display OFF. Further, the setting controller C1b sets the language to Japanese based on the state ID "JP", and sets the number of antennas to be switched in the antenna switching process to ten based on the number ID "00". Still further, the setting controller C1b sets the process speed of the image data by the signal processing circuit 13 to a speed corresponding to the frame rate of 2 fps based on the frame rate ID "00". Similarly, when the radio unit ID is "02JP111140", the setting controller C1b recognizes that the radio unit has one receiving antenna based on the type ID "02", and turns the antenna switching processing OFF and turns the image data display ON. Further, the setting controller C1b sets the process speed of the image data by the signal processing circuit 13 to a speed corresponding to the frame rate of 25 fps.

The radio unit ID actually processed by the setting controller C1b may be digital information in which the type ID, the state ID, the number ID, the frame rate ID, and the serial ID are each 8-bit data. The radio unit ID may be concatenated data consisting of 6 or more IDs. Alternatively, the radio unit ID may not contain separate IDs but a serial number. The process conditions of the main receiving unit may include a process condition to set whether a manipulation of a power switch by the subject is valid or invalid.

As can be seen from the foregoing, the receiving apparatus 2, 22 according to the first embodiment includes the radio unit 2a, 22a and the main receiving unit 2b detachably connected with each other. The radio unit 2a, 22a stores the radio unit ID information 12a, 32a as the identification information to identify the radio unit 2a, 22a itself. The main receiving unit 2b stores the process conditions to perform for each radio unit which can be connected to the main receiving unit 2b in the process condition table 16a which serves as the storage table. The setting controller C1b acquires the radio unit ID information for each connected radio unit, selects the process condition of the main receiving unit 2b corresponding to the acquired radio unit ID information from the process condition table 16a, and sets the selected process condition. Therefore, various radio units can be employed with the same main receiving unit 2b by replacement, and the process condition of the main receiving unit 2b can be automatically and securely set for each radio unit. As a result, the image data supplied from the capsule endoscope 3 can be surely acquired.

Second Embodiment

A second embodiment of the present invention will be described. In the first embodiment described above, the receiving apparatus consists of the radio unit and the main receiving unit directly connected with each other. In the second embodiment, the radio unit and a main receiving device are connected via a cable. A structure including all of the radio unit, the main receiving device, and the cable is employed as a receiving system corresponding to the receiving apparatus.

Figure 5:
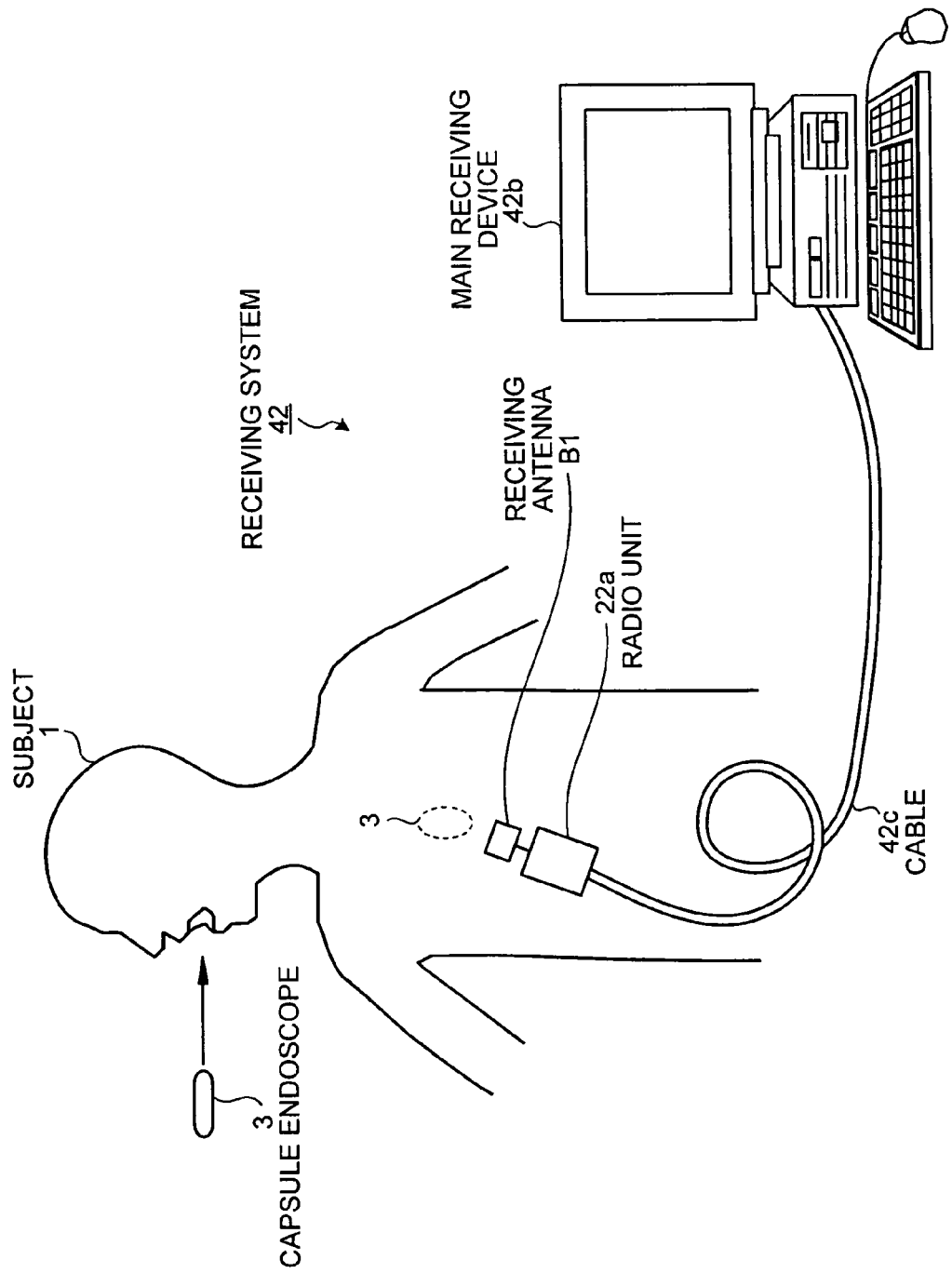
FIG. 5 is a schematic diagram of an overall structure of a wireless in-vivo information acquiring system according to a second embodiment of the present invention.

FIG. 5 is a schematic diagram of an overall structure of a wireless in-vivo information acquiring system according to the second embodiment of the present invention. As shown in FIG. 5, the wireless in-vivo information acquiring system includes a receiving system 42 which has a radio unit 22a in place of the radio unit 2a of the wireless in-vivo information acquiring system of FIG. 1, and a main receiving device 42b in place of the main receiving unit 2b, and a cable 42c connecting the radio unit 22a and the main receiving device 42b. In other respects, the structure of the receiving system of the second embodiment is the same as the structure of the receiving apparatus of the first embodiment, and the same elements will be denoted by the same reference characters.

The cable 42c shown in FIG. 5 is a connector which connects the radio unit 22a that serves as a radio device and the main receiving device 42b. The cable 42c is, for example, a serial cable. The cable 42c is connected to the radio unit 22a and the main receiving device 42b via a connection interface such as RS232C, USB, and IEEE1394, or via an interface such as an extension board, and a PC card.

With reference to FIG. 6, the receiving system 42 will be described. FIG. 6 is a block diagram of a structure of the receiving system 42. As shown in FIG. 6, the receiving system 42 includes the radio unit 22a and the main receiving device 42b. The radio unit 22a and the main receiving device 42b are detachably connected with each other via the cable 42c. The main receiving device 42b is, for example, a workstation or a personal computer, and has a function of receiving the baseband signal demodulated and supplied from the radio unit 22a through the cable 42C and processing the same. A structure corresponding to the main receiving unit 2b includes a control unit C2, a setting controller C2b, the signal processing circuit 13, a display unit 55, a storage unit 56, a process condition table 56a, and a power supply unit 57. Further, the main receiving device 42b includes an input unit 58 which is an input unit such as a keyboard and a mouse. The setting controller C2b acquires radio unit ID information 32a from each radio unit connected to the main receiving device 42b, selects a process condition of the main receiving device 42b corresponding to the acquired radio unit ID information from the storage table stored in the process condition table 56a, and sets the selected process condition as a process condition of the main receiving device 42b.

In the receiving system 42 according to the second embodiment as described above, the radio unit 22a which serves as the radio device and the main receiving device 42b are detachably connected with each other. The radio unit 22a stores the radio unit ID information 32a as the identification information to identify the radio unit 22a itself. The main receiving device 42b stores the process conditions to perform corresponding to each radio unit which may be connected to the main receiving device 42b in the process condition table 56a which serves as the storage table in advance. The setting controller C1b acquires the radio unit ID information of each connected radio unit, selects the process condition of the main receiving device 42b corresponding to the acquired radio unit ID information from the process condition table 56a, and sets the selected process condition as the process condition of the main receiving device 42b. Therefore, different radio units can be employed with the same main receiving device 42b by replacement, and the process condition of the main receiving device 42b can be automatically and securely set for each radio unit. As a result, the image data supplied from the capsule endoscope 3 can be securely acquired. Further, since the receiving system 42 employs an independent computer such as a workstation as the main receiving device 42b, the image data can be displayed on a larger screen than a screen provided in the display unit of the main receiving unit 2b, which is a portable device. Therefore, particularly when the real-time observation is performed on an interior of the body cavity, accuracy in observation and diagnosis can be improved.

In the main receiving device 42b shown in FIG. 6, the control unit C2 including the setting controller C2b, the signal processing circuit 13, and the process condition table 56a are described to be arranged in the main, receiving device. The above elements, however, may be arranged on an extension board, or configured as an external device, and may be connected to the workstation or the like via a predetermined interface when necessary. When such a manner of connection is adopted, versatility and user-friendliness of the receiving system can be improved.

Further, the radio unit and the main receiving unit, and the radio device and the main receiving device may be connected with a photo coupler or the like, so that an optical signal can be transmitted. When such a manner of connection is adopted, insulation between the units or the devices can be improved, and signal noises can be reduced.

Still further, the radio device and the main receiving device may be connected by radio, for example, by an IrDA-compliant infrared communication interface in stead of the cable. The radio device and the main receiving device may be connected via a network such as a Local Area Network (LAN). When such a manner of connection is adopted, the operability and user-friendliness of the receiving system can be improved.

Still further, the power supply unit of the main receiving unit or the main receiving device may consist of a power transformer. When the power transformer is employed, power-supply noise can be reduced.

INDUSTRIAL APPLICABILITY

The receiving apparatus and the receiving system according to the present invention are useful for a receiving apparatus and a receiving system that receive radio signals transmitted from a body insertable device introduced into a subject with the use of an antenna arranged outside the subject, in particular, is suitable for a receiving apparatus and a receiving system that receive radio signals transmitted from a capsule endoscope which serves as the body insertable device.

The invention claimed is:

1. A receiving apparatus comprising:
   a radio unit which includes a storing unit which stores identification information including a plurality of different identification items for identification of the radio unit, and demodulates radio signals received by antennas into base band signals; and
   a main receiving unit which includes a storage table that stores in advance process conditions of a process to be performed by the main receiving unit with respect to each radio unit, each of the process conditions being set based on corresponding one of the identification items, and a setting controller which, when the radio unit is connected to the main receiving unit, acquires the identification information, selects process conditions corresponding to the identification information acquired by referring to the storage table, and sets the selected process conditions as process conditions of the process performed by the main receiving unit, the main receiving unit at least a acquiring information transmitted from the radio unit based on the base band signals.

2. The receiving apparatus according to claim 1, wherein the main receiving unit includes a switching controller which controls switching-over of the antennas based on signal strength of the radio signal received by each of the antennas, the process conditions stored in the storage table include a process condition related to a number of the antennas, and
   the setting controller sets the process condition so that the switching controller controls the switching-over of the antennas based on the process condition related to the number of the antennas.

3. The receiving apparatus according to claim 1, wherein the main receiving unit includes an image display unit which displays image information based on the information transmitted from the radio unit,
   the process conditions stored in the storage table include a process condition about how to output the information received from the radio unit, and
   the setting controller sets the process condition so that the image display unit displays the image information based on the process condition about how to output the information.

4. The receiving apparatus according to claim 1, wherein the main receiving unit includes a processor which performs processes at variable process speed on the information transmitted from the radio unit,
   the process conditions stored in the storage table include a process condition related to a transmission rate of the information, and
   the setting controller sets a process speed of the processor based on the process condition related to the transmission rate of the information.

5. A receiving system comprising:
   a radio device which includes a storing unit which stores identification information including a plurality of different identification items for identification of the radio device, and demodulates radio signals received by an antenna into base band signals;
   a main receiving device which includes a storage table that stores in advance process conditions of a process to be performed by the main receiving device with respect to each radio device, each of the process conditions being set based on corresponding one of the identification items, and a setting controller which, when the radio device is connected to the main receiving device, acquires the identification information, selects process conditions corresponding to the identification information acquired by referring to the storage table, and sets the selected process conditions as process conditions of the process performed by the main receiving device, the main receiving device at least acquiring information transmitted from the radio device based on the base band signals; and a connector which connects the radio device and the main receiving device with each other.

6. The receiving system according to claim 5, wherein
the main receiving device includes an image display unit which displays image information based on the information transmitted from the radio device, the process conditions stored in the storage table include a process condition about how to output the information received from the radio device, and the setting controller sets the process condition so that the image display unit displays the image information based on the process condition about how to output the information.

* * * * *